United States Patent [19]
Whistler

[11] 3,932,625
[45] Jan. 13, 1976

[54] METHOD AND COMPOUND FOR PARASITE CONTROL

[75] Inventor: Roy L. Whistler, West Lafayette, Ind.

[73] Assignee: Purdue Research Foundation, Lafayette, Ind.

[22] Filed: Mar. 25, 1974

[21] Appl. No.: 454,259

[52] U.S. Cl. .............................. 424/180; 260/209 R
[51] Int. Cl.² .......................................... A01N 9/00
[58] Field of Search ................................... 424/180

[56] References Cited
OTHER PUBLICATIONS
Chemical Abstracts, Vol. 78, 1973, p. 261, paragraph 69506 x.

*Primary Examiner*—Elbert L. Roberts
*Assistant Examiner*—Cary Owens

[57] ABSTRACT

A particular compound, namely 5-Thio-D-glucose and use thereof is disclosed herein for parasite control. 5-Thio-D-glucose is administered to effectively deny an energy supply to cells in which parasites are living to thus deny an energy supply to the parasites for eliminating the parasite.

7 Claims, No Drawings

METHOD AND COMPOUND FOR PARASITE CONTROL

FIELD OF THE INVENTION

This invention relates to compound use for parasite control and, more particularly, relates to use of 5-Thio-D-glucose for parasite control.

BACKGROUND OF THE INVENTION

The area of medicine, and particularly that field of human medicine devoted to individual and public health, has long sought a non-toxic compound that could be administered for effective parasite control.

As is known, there are three general types of parasites, namely, intracellular, those that occur in tissues, and those that live in the blood stream. Malaria is a principal example of a type of parasite that lives in the blood stream but it should be noted that malaria can also live in cells.

Intracellular protozoa have been observed to enter host cells in subtle ways, escape the cells digestive processes, and instead have the cell nourishing the parasite, as reported by Professor William Trager in an article entitled "Some Aspects of Intracellular Parasitism" appearing in Science, Volume 183, pages 269–273, Jan. 25, 1974.

As observed by Professor Trager, the environmental requirements and nutritional needs of an intracellular parasite are sufficed only by intact living host cells with the types of intracellular organisms varying over a great range. With respect to particular parasites, it has been observed that some intracellular protozoa appear to enter a host cell by the host cell engulfing the parasite by a phagocytic process, and included in this category are the hemoflagellates of the genus *Leishmania*, for example, which are responsible for a variety of diseases.

The Leishmanial parasites, while entering a host cell without evident activity of the parasite, nevertheless interacts with the cell in a biochemical manner with the cell forming a membrane about the parasite that nourishes the parasite rather than destroying it.

Other intracellular parasites, for example the Toxoplasma gondii, enter host cells by their own activity rather than that of the host cell. This parasite must have a living host cell and can grow and multiply only intracellularly with, again, the host cell being made to nourish the parasite.

Still other intracellular parasites, namely the Microsporida, do not have a membrane formed therearound, but instead form resistent spores with a tubule that extends from the spore and is attached to a host cell so as to be directly in contact with the cytoplasm. Thus, it is not always necessary that the host cell have a membrane around the parasite, as shown again, by example, by erythrocytic malaria, the sporoplasm of Nosema, or the erythrocytic parasite Babesia.

In any event, however, erythrocytic parasites feed by endocytosis and it has been speculated that this may be the general method of feeding by protozoa parasitic in other kinds of cells. By endocytosis feeding, the host cell, of course, at least helps in nourishing the parasite. With respect to the erythrocytic stages of malaria, it is known that the malaria parasite developing within an intact host has relatively few nutritional requirements that must be satisfied from outside the host cell since the host cell provides glucose, a few amino acids, fatty acids and a few vitamins. In fact, the host cell sometimes must modify at least one vitamin before it can be utilized by the parasite. This is true of the malaria parasite P. lophurae which cannot synthesize its own coenzyme A from pantothenic acid and depends upon modification by the host cell. Therefore, the intercellular parasite often finds the host cell to be a true and hospitable host, and the parasite not only exploits the nutrients already available in the cell, but induces the cell to actively assist in nutrition of the parasite.

Since at least some parasites depend upon host cells for nourishment, it is apparent that if the source of the energy to the cell utilized by the parasite can be effectively cut off, then the parasite can be destroyed.

A few years ago, this inventor invented a novel sulfur-containing compound and method for the preparation of the same and U.S. Pat. No. 3,243,425 was issued to me on Mar. 29, 1966, the invention being assigned to Purdue Research Foundation. The sulfur compounds of that invention are based upon the replacement of an oxygen atom in a sugar molecule by a sulfur atom, and, more particularly, are based upon the replacement of the ring oxygen of the sugar by the sulfur atom and oxidized forms of the sulfur atom and thus may be described as thiosugars.

While the compounds described in my U.S. Pat. No. 3,243,425 were recognized to be of both chemical and biochemical interest as sugar analogs, the main recognized use of the compounds was primarily in the preparation of resins by reaction with a diiocyanate or other polyisocyanates, with usefullness as radiation absorbers and as chain terminators in free radical polymerizations being mentioned. More recently, I have found that 5-Thio-D-glucose is also useful as a tumor cell growth restricting compound and as a weight control compound. Patent applications directed to such compound uses have been made the subject matter of U.S. patent applications filed by me on Feb. 14, 1974 and given Ser. Nos. 442,448 and 442,447, respectively. It has remained until now, however, to find and develop usefulness for 5-Thio-D-glucose for parasite control.

SUMMARY OF THE INVENTION

This invention provides a particular compound use for parasite control. 5-Thio-D-glucose has been found to be useful for parasite control by effectively terminating the energy supply to the parasites to thus destroy or aid in destruction of such parasites.

It is therefore an object of this invention to provide a novel compound use for parasite control.

It is another object of this invention to provide a novel use of 5-Thio-D-glucose for parasite control.

It is yet another object of this invention to provide compound use for parasite control by effectively precluding an energy supply to the parasite.

It is still another object of this invention to provide administration of 5-Thio-D-glucose to thereby achieve parasite control.

It is yet another object of this invention to provide a method for parasite control by administering 5-Thio-D-glucose.

With these and other objects in view which will become apparent to one skilled in the art as the description proceeds, this invention resides in the novel composition use thereof substantially as hereinafter described and more particularly defined by the appended claims, it being understood that such changes in the precise embodiment and use of the herein disclosed invention are meant to be included as come within the scope of the claims.

DESCRIPTION OF THE INVENTION

As a result of research, a compound has been found that is useful in parasite control, and this compound is 5-Thio-D-glucose. This compound may be administered to humans and/or animals to preclude an energy supply to the parasites and thus aid in destruction of the same.

The structural formula for 5-Thio-D-glucose is as follows:

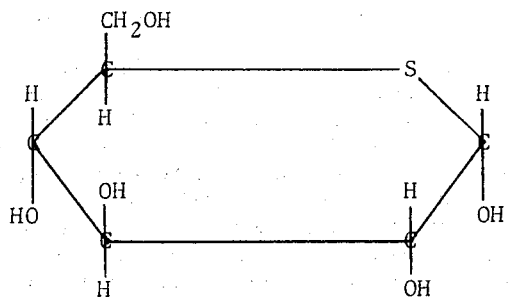

5-Thio-D-glucose is the nearest analog of D-glucose (see U.S. Pat. No. 3,243,425). It may be looked upon structurally as D-glucose in which the ring oxygen atom has been replaced by a sulfur atom. The sugar analog is the nearest analog of D-glucose ever prepared and this analog has nearly the same chemical and physical characteristics as real D-glucose.

While the sugar analog is somewhat sweeter than real D-glucose, it has been found to be non-toxic with an $LD_{50}$ (i.e. a lethal dose as measured by a 50% kill of test animals) of 14,000mg of compound per kg of animal body weight when administered to rats in a single dose. Thus, 5-Thio-D-glucose is suitable for administering to animals and/or humans.

As is known, 5-Thio-D-glucose has the characteristic of inhibiting the transport of real D-glucose across a cell membrane and thus denies carbohydrates to cells and by restricting this energy source causes normal cells to transfer their energy source to fats or proteins. Rapidly developing cells requiring high energy are thus restricted in growth and in multiplication.

Using this characteristic of 5-Thio-D-glucose and the fact that many parasites depend upon a host cell for nourishment, it is believed that many parasites in man and/or animals could be likewise restricted in their source of energy if 5-Thio-D-glucose were supplied to the media surrounding them. Thus, it is my concept and belief that the use of 5-Thio-D-glucose is useful in cutting off the energy, or carbohydrate, supply to at least certain parasites rendering them susceptible to destruction as a consequence of a lack of energy supplied to the parasite or at least making such a parasite susceptible to normal attack by the inherent body protective mechanisms and/or antiparasitic drugs that could be administered in conjunction with 5-Thio-D-glucose to thus destroy the parasite. For example, it is expected that certain parasites living in the blood stream through the years have mutated and adapted themselves to live almost entirely on D-glucose as an energy source. Thus, cutting off this source of supply could lead to destruction of these organisms.

Past experiments have shown by analogy that intercellular parasites would be particularly vulnerable and susceptible to the effects of 5-Thio-D-glucose. As brought out hereinabove, many parasites of the intracellular type depend upon the host cell for nourishment. By providing 5-Thio-D-glucose in the media surrounding the cell, real D-glucose would be denied penetration into the cell where the parasite is living and this would greatly restrict the energy supply to the cell and consequently to the parasite. By thus cutting off the energy supply to the parasite, the normal host cell response could eliminate the parasite by phagocytosis or by other known means. Intracellular parasites are described in Professor Trager's article as set forth hereinabove. It is expected that coccidiosis would, for example, be especially susceptible to destruction by supplying 5-Thio-D-glucose to the cell in which the parasite is living.

In view of the foregoing, it is felt that use of the compound 5-Thio-D-glucose as a novel compound use is effective for parasite control and more particularly to destruction of parasites by restricting the energy source to thereby deny energy to the parasite.

What is claimed is:

1. A method for parasite control which consists essentially of administering to a recipient in which parasites are living at least an effective amount of 5-Thio-D-glucose over a period of time to at least control said parasites.

2. The method of claim 1 wherein said 5-Thio-D-glucose restricts the energy source to a parasite to thus aid in destruction of the same.

3. The method of claim 2 wherein said 5-Thio-D-glucose restricts the energy supply to a host cell of said recipient having a parasite living therein to thereby reduce the energy supplied to such a parasite.

4. The method of claim 3 wherein said 5-Thio-D-glucose is introduced to the media surrounding the parasite to thereby cut off the carbohydrate supply thereto.

5. The method of claim 3 wherein said 5-Thio-D-glucose is administered for destruction of intercellular parasites.

6. The method of claim 1 wherein said 5-Thio-D-glucose is administered in conjunction with anti-parasitic drugs to destroy parasites.

7. The method of claim 1 wherein said 5-Thio-D-glucose prevents penetration of real D-glucose into cells where parasites are living to thereby reduce the energy supplied to the cell and thus aid in destruction of the parasite receiving nourishment from said cell.

* * * * *